(12) United States Patent
Chen et al.

(10) Patent No.: US 10,751,263 B2
(45) Date of Patent: Aug. 25, 2020

(54) DENTAL CEMENT COMPOSITIONS AND METHODS OF USE

(71) Applicant: ZEST IP HOLDINGS, LLC, Carlsbad, CA (US)

(72) Inventors: Xiangxu Chen, Diamond Bar, CA (US); Matthew Marc Durban, Fullerton, CA (US); Lingyan Julia Wang, Irvine, CA (US)

(73) Assignee: ZEST IP HOLDINGS, LLC, Carlsbad, CA (US)

( * ) Notice: Subject to any disclaimer, the term of this patent is extended or adjusted under 35 U.S.C. 154(b) by 4 days.

(21) Appl. No.: 15/944,680

(22) Filed: Apr. 3, 2018

(65) Prior Publication Data

US 2018/0289593 A1 Oct. 11, 2018

Related U.S. Application Data

(60) Provisional application No. 62/481,005, filed on Apr. 3, 2017.

(51) Int. Cl.
| | | |
|---|---|---|
| *A61K 6/083* | (2006.01) | |
| *A61K 6/889* | (2020.01) | |
| *A61K 6/19* | (2020.01) | |
| *A61K 6/40* | (2020.01) | |
| *A61K 6/79* | (2020.01) | |

(52) U.S. Cl.
CPC .............. *A61K 6/889* (2020.01); *A61K 6/19* (2020.01); *A61K 6/40* (2020.01); *A61K 6/79* (2020.01)

(58) Field of Classification Search
CPC ................................ A61K 6/005; A61K 6/887
See application file for complete search history.

(56) References Cited

U.S. PATENT DOCUMENTS

| | | | |
|---|---|---|---|
| 5,256,065 A | 10/1993 | Nicholson | |
| 2006/0189728 A1* | 8/2006 | Qian | A61K 6/0023 524/99 |
| 2007/0040151 A1* | 2/2007 | Utterodt | A61K 6/0017 252/182.13 |
| 2010/0028835 A1* | 2/2010 | Hansen | A61C 13/083 433/218 |
| 2010/0130682 A1* | 5/2010 | Hinamoto | A61K 6/0023 524/854 |
| 2016/0081885 A1 | 3/2016 | Neffgen et al. | |

FOREIGN PATENT DOCUMENTS

| | | |
|---|---|---|
| EP | 1479364 B1 | 11/2004 |
| WO | 2008134024 A2 | 11/2008 |

OTHER PUBLICATIONS

Optibond® SDS, Kerr Corporation, Nov. 25, 2013. (Year: 2013).*
International Search Report and Written Opinion for PCT/US2018/025955, dated Aug. 2, 2018, 11 pages.

* cited by examiner

*Primary Examiner* — Michael F Pepitone
(74) *Attorney, Agent, or Firm* — Procopio, Cory, Hargreaves & Savitch LLP; Robert T. Ramos

(57) ABSTRACT

Provided herein are dental compositions and methods for use in dental cementation applications.

8 Claims, No Drawings

DENTAL CEMENT COMPOSITIONS AND METHODS OF USE

RELATED APPLICATIONS

This application claims the benefit of U.S. Provisional Application No. 62/481,005, filed on Apr. 3, 2017, and the contents of the aforementioned application are incorporated herein by reference in their entirety.

FIELD OF THE INVENTION

The field of use is dental compositions, particularly those useful in dental cementation applications.

BACKGROUND OF THE INVENTION

A dental restoration or dental filling is a dental restorative material used to restore the function, integrity and morphology of missing tooth structure. The structural loss typically results from caries or external trauma (collectively referred to herein as cavities). It is also lost intentionally during tooth preparation to improve the aesthetics or the physical integrity of the intended restorative material.

Dental cements are used for a variety of dental and orthodontic applications, including use as luting agents, pulp-protecting agents or cavity-lining material. Furthermore, they are used to form an insulating layer under metallic, resin or ceramic restorations, and protect the pulp from injury. This helps in sealing or fixing and casting inlays, onlays, or any such substance to both dentin and enamel.

Resin cements usually have two categories: total-etch and self-adhesive resin cements. For proper use, pure resin cements require pretreatment of the tooth surface, preferably with phosphoric acid and application of a dentin and enamel primer prior to application of the resin cement. After curing this forms a micromechanical bond to both dentin and enamel. Also, they are insoluble in oral fluids. There are 2 types of these "traditional resin cements" (those that require the use of the "total-etch technique and dentin adhesive technology") that are commonly used—dual-cured and light-cured versions. The most recent addition to the "resin cement family" are the self-adhering resin cements that require no pretreatment of the tooth surface and appear to have many of the clinical advantages of traditional resin cement systems, with the ease of use of more traditional types of cements. It is important to note that, in general, bond strengths of self-etching resin cements are not as high as those for resin cements using the total-etch technique and, as a result, may more likely lead to microleakage at the margin.

An ideal dental cementation material may provide strong and durable cementation and ease of use.

SUMMARY OF THE INVENTION

Provided herein, in certain embodiments, are dental compositions comprising a polymerizable monomer, and a hydroperoxide and/or thiourea. In some embodiments, the compositions further comprise copper (II) (e.g., as a catalyst).

Also provided herein is a dental composition, wherein said composition comprises, on a surface of a dental substrate, a bonding agent; and a paste mixture, wherein the bonding agent comprises at least one phosphoric acid containing (meth)acrylic monomer, wherein the paste mixture at least one polymerizable monomer, at least one hydroperoxide; and at least one thiourea compound. The phosphoric acid containing (meth)acrylic monomer is selected from the group consisting of GPDM (glycerol phosphate di(meth)acrylate{(meth)acrylate=acrylate or methacrylate}), phenyl-P (phenyl methacryloxyethyl phosphate), PENTA-P (dipentaerithritol pentaacrylate phosphate), 10-MDP (methacryloyloxydecyl phosphate), HEMA-P (hydroxyethylmethacrylate phosphate), HEA-P (hydroxyethylacrylate phosphate), bis(HEMA)-P {bis(hydroxyethylmethacrylate) phosphate}, bis(HEA)-P {bis(hydroxyethylacrylate) phosphate}, bis((meth)acryloxypropyl)phosphate, and combinations thereof. In a particular embodiment, the phosphoric acid containing (meth)acrylic monomer is 10-Methacryloyloxydecyl dihydrogen phosphate (10-MDP). The thiourea is selected from the group consisting of 1-(2-Pyridyl)-2-thiourea (PTU), 1-Benzoyl-2-thiourea (BTU), 1-Acetyl-2-thiourea (ATU), 1-(2-Tetrahydrofurfuryl)-2-thiourea (TTU), or a combination thereof. In a particular embodiment, the thiourea is 1-(2-Pyridyl)-2-thiourea (PTU). In particular embodiments, the hydroperoxide is a tertiary hydroperoxide. In particular embodiments, either the first part or second part of the paste mixture further comprises a copper (II) compound. In a particular embodiment, the dental substrate is Zirconia. In another embodiment, the bonding agent is a single bottle bonding agent.

Also provided herein, is a method of dental restoration, wherein said method comprises: a first step of applying a dental bonding agent on a dental substrate, wherein the bonding agent comprises at least one phosphoric acid containing (meth)acrylic monomer; and a second step of applying paste mixture from a device having a first part and a second part separate from each other, wherein said first part and second part form the past mixture, and wherein the paste mixture from the device comprises at least one polymerizable monomer and at least one hydroperoxide in the first part; and at least on thiourea compound in the second part. In particular embodiments, the phosphoric acid containing (meth)acrylic monomer is selected from the group consisting of GPDM (glycerol phosphate di(meth)acrylate{(meth)acrylate=acrylate or methacrylate}), phenyl-P (phenyl methacryloxyethyl phosphate), PENTA-P (dipentaerithritol pentaacrylate phosphate), 10-MDP (methacryloyloxydecyl phosphate), HEMA-P (hydroxyethylmethacrylate phosphate), HEA-P (hydroxyethylacrylate phosphate), bis(HEMA)-P {bis(hydroxyethylmethacrylate) phosphate}, bis(HEA)-P {bis(hydroxyethylacrylate) phosphate}, bis((meth)acryloxypropyl)phosphate, and combinations thereof. In a particular embodiment, the phosphoric acid containing (meth)acrylic monomer is 10-Methacryloyloxydecyl dihydrogen phosphate (10-MDP). The thiourea is selected from the group consisting of 1-(2-Pyridyl)-2-thiourea (PTU), 1-Benzoyl-2-thiourea (BTU), 1-Acetyl-2-thiourea (ATU), 1-(2-Tetrahydrofurfuryl)-2-thiourea (TTU), or a combination thereof. In a particular embodiment, the thiourea is 1-(2-Pyridyl)-2-thiourea (PTU). In particular embodiments, the hydroperoxide is a tertiary hydroperoxide. In particular embodiments, either the first part or second part of the paste mixture further comprises a copper (II) compound. The bonding agent bonds effectively on a dental substrate. In a particular embodiment, the dental substrate is Zirconia. In particular embodiments, the bond strength of the dental bonding agent on a dental substrate is more than 15 MPa. In one embodiment, the device is a dual-barrel syringe.

Also provided is a dental composition, wherein said composition comprises, on a surface of a dental substrate, a bonding agent; and a paste mixture, wherein the bonding agent comprises at least one phosphoric acid containing (meth)acrylic monomer, wherein the paste mixture was formed by mixing together a previously separated first part and a second part, and wherein the first part comprises at least one polymerizable monomer and at least one hydroperoxide; and the second part comprises at least one thiourea compound. In a particular embodiment, the previously separated first part and a second part were separated in a dual-barrel syringe.

In other embodiments the dental composition comprises a first part and a second part, the first part comprising: a copper (II) catalyst; a hydroperoxide; and a polymerizable monomer, the polymerizable monomer comprising an ethylenic group, and the second part comprising: a copper (II) catalyst; a thiourea; and a polymerizable monomer, the polymerizable monomer comprising an ethylenic group. In specific embodiments, the first and second parts are physically separated (e.g., until such a time as the dental composition is used to restore a cavity in a tooth).

In some embodiments, provided herein is a dental composition comprising a first and a second part, the first and second part collectively comprising: a copper (II) catalyst; a hydroperoxide; a polymerizable monomer, the polymerizable monomer comprising an ethylenic group; and a thiourea. In specific embodiments, the first part comprises the hydrogen peroxide, the second part comprises the thiourea, and the first and the second part are physically separated from each other (e.g., until such a time as the dental composition is used to restore a cavity in a tooth).

In some embodiments, provided herein is a dental composition, a part thereof, or a resin precursor thereof, wherein said composition comprises: a copper (II) catalyst; a hydroperoxide; and a polymerizable monomer (e.g., the polymerizable monomer comprising an ethylenic group). Similarly, in certain embodiments, provided herein is a dental composition, a part thereof, or a resin precursor thereof, wherein said composition comprises: a copper (II) catalyst; a thiourea; and a polymerizable monomer (e.g., the polymerizable monomer comprising an ethylenic group).

In some embodiments, provided herein is a dental composition (e.g., a fast curing, copper free, acid free composition) comprising a first and a second part, the first and second part collectively comprising: a hydroperoxide (e.g., the hydroperoxide being a tertiary aryl hydroperoxide (e.g., HOOCR'$_3$, wherein each R' is independently alkyl or aryl, with at least one R' being aryl (e.g., substituted or unsubstituted aryl), such as cumenehydroperoxide); a polymerizable monomer (e.g., the polymerizable monomer comprising an ethylenic group); and a thiourea. In some embodiments, the first part comprises the hydrogen peroxide, the second part comprises the thiourea, and the first and the second parts are physically separated from each other. In specific embodiments, the hydroperoxide has a concentration in the dental composition of about 1.5% (w/w) or more or a concentration relative to the monomer of about 1.5% (w/w) or more. In more specific embodiments, the hydroperoxide has a concentration in the dental composition of about 2% (w/w) or more or a concentration relative to the monomer of about 2% (w/w) or more. In still specific embodiments, the hydroperoxide has a concentration in the dental composition of about 2.5% (w/w) or more or a concentration relative to the monomer of about 2.5% (w/w) or more. In further or alternative embodiments, the thiourea has a concentration in the dental composition of about 1.5% (w/w) or more or a concentration relative to the monomer of about 1.5% (w/w) or more. In more specific embodiments, the thiourea has a concentration in the dental composition of about 2% (w/w) or more or a concentration relative to the monomer of about 2% (w/w) or more. In still specific embodiments, the thiourea has a concentration in the dental composition of about 2.5% (w/w) or more or a concentration relative to the monomer of about 2.5% (w/w) or more. In further or additional embodiments, the combined weight of the hydroperoxide plus thiourea has a concentration in the dental composition of about 3% (w/w) or more or a concentration relative to the monomer of about 3% (w/w) or more. In more specific embodiments, the combined weight of the hydroperoxide plus thiourea has a concentration in the dental composition of about 4% (w/w) or more or a concentration relative to the monomer of about 4% (w/w) or more. In still specific embodiments, the combined weight of the hydroperoxide plus thiourea has a concentration in the dental composition of about 5% (w/w) or more or a concentration relative to the monomer of about 5% (w/w) or more.

In certain embodiments, the copper (II) catalyst comprises a copper (II) ion and/or a copper (II) compound. In specific embodiments, the copper (II) catalyst comprises copper (II) sulfate, copper (II) acetate, copper (II) chloride, copper (II) acetylacetonate, or a combination thereof. In some embodiments, the copper (II) catalyst is present in the composition in an amount of about 5 wt. % or less (e.g., about 1 wt % or less, or about 0.1 wt. % or less).

In some embodiments, the hydroperoxide comprises a hydrocarbon (e.g., $C_4$-$C_{20}$ hydrocarbon) substituted with one or more —OOH group. In specific embodiments, the hydroperoxide is a tertiary hydroperoxide (e.g., the —OOH group is substituted with a carbon having tertiary substitution). In more specific embodiments, the hydroperoxide is or comprises t-butyl hydroperoxide, t-amyl hydroperoxide, p-diisopropylbenzenehydroperoxide, cumenehydroperoxide, pinanehydroperoxide, p-menthanehydroperoxide, and 1,1,3,3-tetramethylbutyl hydroperoxide, or a combination thereof. In further or alternative embodiments, the hydroperoxide is present in the composition in an amount of about 0.01% (w/w) to about 10% (w/w). In more specific embodiments, the hydroperoxide is present in the composition in an amount of about 0.1% (w/w) to about 5% (w/w). In some embodiments, the hydroperoxide is present in the composition in a ratio of hydroperoxide to polymerizable monomer of about 1:9999 to about 1:9. In more specific embodiments, the ratio of hydroperoxide to polymerizable monomer is about 1:99 to about 5:95.

In certain embodiments, the monomer is a dentally acceptable monomer. In some embodiments, the monomer comprises a vinyl, an acrylate, a methacrylate, or a combination thereof. In further or alternative embodiments, the monomer is present in an amount of about 10% (w/w) to about 60% (w/w). In more specific embodiments, the polymerizable monomer is present in an amount of about 20% (w/w) to about 50% (w/w).

In certain embodiments, the thiourea comprises 1-(2-Pyridyl)-2-thiourea (PTU), 1-Benzoyl-2-thiourea (BTU), 1-Acetyl-2-thiourea (ATU), 1-(2-Tetrahydrofurfuryl)-2-thiourea (TTU), or a combination thereof. In further or alternative embodiments, the thiourea is present in the composition in a ratio of thiourea to polymerizable monomer of about 1:999 to about 100:900. In more specific embodiments, the ratio of thiourea to polymerizable monomer is about 1:99 to about 10:90.

In specific embodiments, a dental composition provided herein comprises a filler. In more specific embodiments, the first and second parts comprise a filler. In still more specific embodiments, the filler is a finely divided filler. In some embodiments, the finely divided filler comprises a plurality of particles. In specific embodiments, the particles having an average dimension (e.g., diameter) of about 0.02 microns to about 30 microns, e.g., about 0.2 microns to about 10 microns. In further or alternative embodiments, the filler comprises an inorganic filler, a pre-polymerized filler, or a combination thereof. Fillers include, by way of non-limiting example, metal oxide, a metal nitride, a metal fluoride, a silicate, silica (e.g., colloidal silica, precipitated silica, fused silica), an aluminosilicate, an aluminoborosilicate, a fluoroaluminosilicate, a bariumsilicate, a bariumaluminosilicate, a barium aluminoborosilicate, a strontiumaluminosilicate, a bariumfluoroaluminosilicate, a strontiumfluoroaluminosilicate, a strontiumzincfluoroaluminosilicate, a zinc aluminosilicate, a pre-polymerized filler, and a combination thereof. In some embodiments, the filler is present in an amount of about 10% (w/w) to about 90% (w/w). In more specific embodiments, the filler is present in an amount of about 40% (w/w) to about 80% (w/w). In still more specific embodiments, the filler is present in an amount of about 60% (w/w) to about 80% (w/w).

In some embodiments, the composition comprises a photoinitiator, a stabilizer, a solvent, or any combination thereof. In some embodiments, a photoinitiator is present in an amount of about 5% (w/w) or less. In further or alternative embodiments, a stabilizer is present in an amount of about 1% (w/w) or less.

In some embodiments, a composition provided herein is free of, or substantially free of, an acid or anhydride. In specific embodiments, the composition (and/or part(s) thereof) comprises less than 5% (w/w) of an acid (e.g., less than 3% (w/w), less than 1% (w/w), or less than 0.5% (w/w)). In particular embodiments, the composition, or parts thereof, is non-acidic (e.g., having a pH of about 5 or more).

In various embodiments, compositions provided herein have good performance characteristics, such as when utilized in restorative dental applications (e.g., in restoring a tooth with a Class I or Class II cavity). In specific embodiments, upon combination of the first and second parts, the total volume of the composition shrinks by less than 10% (e.g., less than 8%, less than 6%, or less than 4%)(e.g., as it sets). In some instances, minimizing such shrinkage reduces the incidences of void formation between a filling and a tooth, reduces incidences of damage (e.g., cracking) to the tooth during and following restoration, and the like. In further or alternative embodiments, upon combination of the first and second parts, the hygroscopicity of the composite is less than 100 μg/mm$^3$ (e.g., less than 50 μg/mm$^3$, less than 25 μg/mm$^3$, less than 20 μg/mm$^3$, or less than 15 μg/mm$^3$). In some instances, minimizing the hygroscopicity reduces expansion of the restoration material following curing to a resultant composite which, in turn, may reduce incidences of damage (e.g., cracking) to the tooth, dislodgement of the filling from the tooth, and/or the like.

Also provided herein are dental composites resulting from the mixing of composition components or parts described herein, e.g., partially or wholly cured mixtures. In some embodiments, the composite comprises a partially or wholly cured resin, filler and copper. In specific embodiments, the composite comprises the cured resin in an amount of about 10% (w/w) to about 60% (w/w), the filler in an amount of about 10% (w/w) to about 90% (w/w), and the copper in an amount of about 1 elemental wt. % or less. Also provided herein is a reaction mixture comprising a copper (II) catalyst; a hydroperoxide; a polymerizable monomer, the polymerizable monomer comprising an ethylenic group; and a thiourea. The reaction mixture may be partially cured, with a portion of the monomeric units thereof forming monomers and other portions forming oligomer or polymers thereof.

In some embodiments, two part compositions provided herein are contained within a dual chambered device comprising a housing body, the housing body comprising a first chamber and a second chamber, the first chamber containing the first part of a composition described herein, the second chamber containing the second part of a composition described herein. In specific embodiments, dual chambered device is configured to concomitantly extrude and/or mix the first and second parts.

Also provided herein is a method for restoring a tooth in an individual. In some embodiments, the process comprises combining a first composition (e.g., a first part of a dental composition described herein) with a second composition (e.g., a second part of a dental composition described herein) to form a mixed composition. In specific embodiments, the first composition comprising a hydroperoxide, the second composition comprising a thiourea, and one or both of the first and/or second compositions comprising a copper (II) catalyst, a polymerizable monomer (e.g., the polymerizable monomer comprising an ethylene group), and a filler. In some embodiments, the method further comprises administering the mixed composition to an individual (e.g., to a Class I or Class II cavity in a tooth of the individual). In some embodiments, the process further comprises curing the mixed composition (e.g., allowing the composition to self-cure, and/or using a dental curing light to photo-cure the composition). In specific embodiments, curing of the mixed composition results in the formation of a restoration composite (e.g., in the form of a filling within a dental cavity of the individual). In preferred embodiments, the curing step (e.g., self-curing) occurs relatively quickly in order to facilitate the restoration process. In specific embodiments, the curing step (e.g., self-curing or setting) occurs within 10 minutes, within 4 minutes, within 2 minutes, or the like.

In a particular embodiment, the invention method comprises the steps of: 1) applying a dental bonding primer on dentin and enamel (e.g., the tooth structure), optionally followed by a curing activator, optionally curing the primer layer with a dental curing light; 2) applying a dental bonding primer on prefabricated restorations, such as crowns, inlays, onlays, veneers, optionally followed by a curing activator, optionally curing the primer layer with a dental curing light; 3) applying a dental cement layer to bond prefabricated restorations to the tooth structure (dentin and enamel).

In some embodiments, the method comprises removing decay from in and around a cavity to be filled (e.g., drilling the tooth to remove decay therefrom).

These and other objects, features, and characteristics of the compositions, parts thereof, precursors thereof, resultant composites, and methods disclosed herein, as well as the methods of manufacture, will become more apparent upon consideration of the following description and the appended claims with reference to the accompanying drawings, all of which form a part of this specification. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE INVENTION

Provided herein are dental compositions. Also provided herein are component parts thereof, dental restoration processes, resins used in the preparation of dental compositions, dental composites (e.g., filling materials), and the like. In specific embodiments, the dental compositions comprise two parts, such as two parts that are kept physically separated from each other. In some instances, when the two parts are combined, such as when the dental composition is used in a dental restoration process (such as described herein), the composition forms a composite (e.g., a filling material used in tooth restoration).

In particular embodiments, provided herein is a dental composition comprising two parts (e.g., with free radical polymerization being initiated upon the mixing thereof), the two part dental composition comprising, in some embodiments: (1) at least one monomer with at least one ethylenically unsaturated group (e.g., also referred to herein as a polymerizable monomer comprising an ethylenic group, such as described herein); (2) one part comprising at least one hydroperoxide group; and (3) one part comprising at least one substituted thiourea. In more specific embodiments, the two part dental composition comprises: (1) at least one monomer with at least one ethylenically unsaturated group; (2) one part comprising at least one hydroperoxide group; (3) one part comprising at least one substituted thiourea; (4) at least one part comprising at least one copper (II) compound (e.g., a copper (II) compound that catalyzes, such as, facilitates and/or speeds up curing of the composition (e.g., polymerization of the monomeric components thereof) upon combination of the first and second parts).

In specific embodiments, provided herein is a dental composition comprising a first and a second part, the first part comprising: (1) a copper (II) catalyst; (2) a hydroperoxide; and (3) a polymerizable monomer comprising an ethylenic group, and the second part comprising: (1) a copper (II) catalyst; (2) a thiourea; and (3) a polymerizable monomer comprising an ethylenic group. Also provided herein are the individual first and second parts thereof, including, e.g., a dental composition comprising (1) a copper (II) catalyst; (2) a hydroperoxide; and (3) a polymerizable monomer comprising an ethylenic group, and/or a dental composition comprising (1) a copper (II) catalyst; (2) a thiourea; and (3) a polymerizable monomer comprising an ethylenic group.

In certain embodiments, provided herein is a dual chambered device comprising a housing body, the housing body comprising a first chamber and a second chamber, the first chamber containing therein the first part of a composition described herein, and the second chamber containing therein the second part of a composition provided herein. In some embodiments, the dual chambered device is any suitable device suitable for concomitantly extruding the first and second parts, such as to allow the mixing of the first and second parts and facilitate initiation and polymerization of the monomeric component(s) thereof. In specific embodiments, the dual chambered device is a dual barreled syringe comprising a nozzle configured to facilitate mixing of the first and second parts upon (concurrent) depression of a comprising a first and second plunger.

In certain embodiments, the monomer with at least one ethylenically unsaturated group or polymerizable monomer comprising an ethylenic group is a compound comprising at least one >C=C<group. In specific embodiments, the monomer is represented by the formula $R_2C=CR_2$, wherein each R is independently selected from H, $COOR^1$, or an optionally substituted hydrocarbon, such as alkyl, aryl, or the like, such as wherein at least one R is not H. In specific embodiments, at least one R is $COOR^1$ or an aryl (e.g., phenyl, or the like). In some embodiments, $R^1$ is either H or alkyl (e.g., $C_1$-$C_6$ alkyl). In more specific embodiments, the alkyl is a $C_1$-$C_6$ alkyl (e.g., methyl, ethyl, or the like). In certain embodiments, an alkyl is an acyclic (e.g., branched or straight chain) or cyclic, saturated or unsaturated alkyl. In some embodiments, optional substituents include, by way of non-limiting example, —OH, alkyl, and/or aryl. In certain embodiments, the monomer comprises one or more moiety represented by the formula $R_2C=CRL$, wherein the R and L groups are independently as described for the R groups above. In certain embodiments, a monomer comprises two or more $R_2C=CRL$ groups, wherein the L groups are linked together (e.g., as $R_2C=CRL$-$(LCR=CR_2)_a$, wherein a>0, such as 1-5, e.g., 1-2), such as illustrated in Formula I:

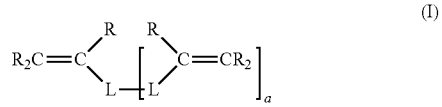

(I)

For example, in some embodiments, the monomer is optionally $R_2C=CR-COO((CH_2)_m(CHOH)_n)_pOOC-RC=CR_2$, wherein m is 1-6 (e.g., 2-4), n is 0-1, and p is 1-30 (e.g., 1-10).

In specific embodiments, the monomer is an acrylate (e.g., wherein three R groups=H and one R group=$COOR^1$), a methacrylate (e.g., wherein two R groups=H, one R group=methyl, and another R group (on the same carbon as the methyl) is $COOR^1$), or a vinyl group (wherein at least one R group is a hydrocarbon). In some embodiments, the monomer comprises an acrylate, a methacrylate, and/or a vinyl group. In specific embodiments, the ethylenically unsaturated group is selected from acrylate and methacrylate groups. Examples of polymerizable monomers include, but are not limited to, the following: glycerol di(meth)acrylate, glycerol mono(meth)acrylate, hydroxyethyl (meth)acrylate {(meth)acrylate=acrylate or methacrylate}, hydroxypropyl (meth)acrylate, methyl (meth)acrylate, ethyl (meth)acrylate, propyl (meth)acrylate, octyl (meth)acrylate, decyl (meth)acrylate, 2-ethoxyethyl (meth)acrylate, 2'-ethoxy-2-ethoxyethyl (meth)acrylate, ethyleneglycol di(meth)acrylate, diethyleneglycol di(meth)acrylate, triethyleneglycol di(meth) acrylate; polyethyleneglycol mono-(meth)acrylate, polyethyleneglycol di-(meth)acrylate, polypropyleneglycol mono-(meth)acrylate, polypropyleneglycol di-(meth)acrylate, polytetramethyleneglycol mono-(meth)acrylate, polytetramethyleneglycol di-(meth)acrylate, hexanediol di(meth)acrylate, octanediol di(meth)acrylate, decanediol di(meth)acrylate, trimethyloylpropane tri(meth)acrylate, urethane dimethacrylate (reaction adduct of 2-hydroxyethyl methacrylate with 2,4,4-trimethylhexane diisocyanate), 2,2-bis[4-(2-hydroxy-3-methacryloylpropoxy)-phenyl]-propane (Bis-GMA), ethoxylatedbisphenol A dimethacrylate (where total number of moles of ethylene oxide in the molecule may range from 2 to 30 units) in tetrahydrofurfuryl (meth)acrylate, or mixtures thereof. As referred to herein, "(meth)acrylate" includes disclosures of both methacrylate and acrylate.

In certain embodiments, the amount of monomer present in the composition is any suitable amount. In certain embodiments, a dental composition provided herein comprises monomer in a weight percentage (e.g., of the total composition) amount between 10% and 60%. In more specific embodiments, the weight percentage is between 20% and 50%.

In certain embodiments, compositions provided herein comprise copper (II), such as in the form of a copper (II) compound. In specific instances, copper(II) (e.g., a copper (II) compound) is utilized to catalyze curing (e.g., hardening, or otherwise setting) of the composition (e.g., accelerate or otherwise facilitate polymerization of the monomer). In specific instances, the presence of the copper (II) (e.g., compound thereof) accelerates the polymerization process when two parts of the inventive composition are mixed (e.g., whereby separated hydroperoxide and thiourea come together and facilitate initiation of polymerization, which is accelerated by the presence of the copper (II)). A copper (II) catalyst is optionally in a disassociated, associated (e.g., in the form of a copper (II) compound), or partially associated form. In various embodiments, the copper (II) compound is any suitable compound that comprises at least one copper (II) in its molecular formula. Examples of copper (II) compounds include, but are not limited to, copper (II) sulfate, copper (II) acetate, copper (II)chloride, copper (II) acetylacetonate, and combinations thereof. In specific embodiments, the copper (II) compound is copper (II) acetate. In other embodiments, the said copper (II) compound is copper (II) acetylacetonate. In specific embodiments, the weight percentage of the copper (II) (or compound thereof) is less than 1%. In more specific embodiments, the weight percentage of the copper (II) (or compound thereof) is less than 0.1%. In still more specific embodiments, the copper (II) (or compound thereof) is provided in, or combined in, a composition herein in an amount of about 0.001 wt. % to about 0.05 wt %.

In certain embodiments, the hydroperoxide is any suitable agent, particularly a dentally acceptable agent, such as that when combined with a thiourea provided herein initiates and/or otherwise facilitates polymerization of the monomer herein, such as at a rate suitable for dental applications, particularly restorative applications. In some embodiments, the hydroperoxide is represented by the formula HOO—$R^2$, wherein $R^2$ is any suitable organic group. In specific embodiments, $R^2$ is a hydrocarbon, such as a $C_4$-$C_{20}$ hydrocarbon (optionally substituted with any suitable groups, such as alkyl groups, aryl groups (e.g., phenyl), alkylaryl groups, additional —OOH groups, and/or the like). In some embodiments, $R^2$ is represented by the formula: —$CR^3R^4R^5$, wherein each of $R^3$, $R^4$, and $R^5$ are independently H, alkyl (cyclic and/or acyclic, and branched or straight chain), aryl (e.g., phenyl), arylalkyl (e.g., attached to the carbon at the alkyl), alkylarylalkyl, or the like, wherein such groups are optionally substituted or unsubstituted. In some embodiments, at least two of $R^3$, $R^4$, and $R^5$ are not H. In specific embodiments, the hydroperoxide is a tertiary hydroperoxide, i.e., wherein none of $R^3$, $R^4$, and $R^5$ are H. In certain instances, any one or more of $R^3$, $R^4$, and/or $R^5$ are optionally taken together with another or both of $R^3$, $R^4$, and $R^5$ to form a cyclic (mono or polycyclic) alkyl group (which is optionally substituted or unsubstituted, such as discussed herein). As discussed herein, any suitable hydroperoxide compound with at least one hydroperoxide group is optionally used. In specific embodiments, the hydroperoxide compound comprises more than one hydroperoxide group. Non-limiting examples of hydroperoxide compounds include, but are not limited to, t-butyl hydroperoxide, t-amyl hydroperoxide, p-diisopropylbenzenehydroperoxide, cumenehydroperoxide, pinanehydroperoxide, p-methane hydroperoxide, and 1,1,3,3-tetramethylbutyl hydroperoxide.

In some embodiments, any suitable concentration of hydroperoxide is optionally utilized in the compositions and methods provided herein. In specific embodiments, the total hydroperoxide compound(s) is in the range of about 0.01% (w/w) to about 10.0% (w/w) (e.g., of the overall composition). In certain embodiments, the hydroperoxide is present in the range of about 0.1% (w/w) to about 5.0% (w/w) of the overall composition. In some embodiments, the hydroperoxide is present in the composition in an amount of about 1.5% (w/w) to about 5% (w/w). In certain instances, hydroperoxides provided herein, such as amongst those described above, are stable under a variety of conditions and have a long shelf-life.

Any suitable thiourea is optionally utilized in a compositions described herein (e.g., in at least one part of a two-part composition described herein). In some embodiments, the thiourea is a substituted thiourea, such as a dentally acceptable thiourea. In some embodiments, the thiourea is an organic thiourea, e.g., a thiourea substituted with an organic radical (e.g., a pyridyl, acetyl, or the like). In specific embodiments, the thiourea is represented by the structure $R^6R\ NC(=S)NR^8R^9$, wherein $R^6$, $R^7$, $R^8$, and $R^9$ are independently selected from H, $COR^{10}$, heterocycloalkyl and heteroaryl (e.g., the heterocycloalkyl or heteroaryl being substituted or unsubstituted), $R^{10}$ being an alkyl, heteroalkyl (cyclic or acyclic), aryl, or heteroaryl ($R^{10}$ being substituted or unsubstituted). In specific embodiments, the thiourea group is attached to the heterocycloalkyl or heteroaryl at a carbon alpha to a heteroatom of the ring. In some embodiments, at least one of or one of $R^6$, $R^7$, $R^8$, and $R^9$ is not H. In specific embodiments, the substituted thiourea is selected from the group consisting of 1-(2-Pyridyl)-2-thiourea (PTU), 1-Benzoyl-2-thiourea (BTU), 1-Acetyl-2-thiourea (ATU), 1-(2-Tetrahydrofurfuryl)-2-thiourea (TTU) and any mixture thereof (i.e., any one or more of PTU, BTU, ATU, and/or TTU).

In certain embodiments, combination of the two parts of the composition provided herein results in curing of the composition. In specific instances, combination of the two parts, particularly the hydroperoxide and the thiourea thereof, facilitates initiation of polymerization of the monomer component of the composition. In certain embodiments, inclusion of the copper (II) catalyst accelerates the curing process (e.g., polymerization of the monomer component(s)), resulting in a set time that is fast enough to be suitable for dental applications. In some instances, when the two-parts are mixed, the mixed composition cures (e.g., sets or hardens). In one embodiment, the setting time is less than 20 minutes (e.g., without the need for photo-curing using a photo-curing device emitting a majority of light having a wavelength in the blue range (e.g., 400 nm to 530 nm, such as about 470 nm)). In one embodiment, the setting time is less than 10 minutes. In one embodiment, the setting time is less than 5 minutes. In more preferred embodiments, the cure (e.g., set) time is about 250 seconds or less. In preferred embodiments, the cure (e.g., set) time is about 180 seconds or less. In further or alternative embodiments, the composition, when the two parts are combined, has a work time of about 200 seconds or less, e.g., about 150 seconds or less. Further, in some embodiments, the work time is at least 30 seconds (e.g., to allow restoration or filling of a tooth cavity, particularly a Class I or Class II cavity).

In certain embodiments, additional additives are included in the composition and/or parts thereof. In some embodiments, any suitable additive is optionally included, such as, by way of non-limiting example, a photo-initiator, a filler, a stabilizer, a solvent, or a combination thereof. In specific embodiments, a dental composition (or part thereof) comprises a resin composition and a filler (e.g., the resin composition comprising the materials of a dental composition described herein). In more specific embodiments, each part of a composition provided herein comprises a resin composition (e.g., a composition comprising monomer described herein) and filler.

In specific embodiments, a composition (or part thereof) provided herein comprises a filler, e.g., at least one finely divided filler. In some instances, a filler may reduce polarization shrinkage, improve mechanical properties and increase radiopacity of a dental composite. In further or alternative instances, a filler may change the rheological properties of a dental composition. Exemplary fillers include, but are not limited to, metal oxides, metal nitrides, metal fluorides, silicate glass, colloidal silica, precipitated silica, fused silica, aluminosilicate glass, aluminoborosilicate glass, fluoroaluminosilicate glass, bariumsilicate, bariumaluminosilicate, bariumaluminoborosilicate, strontiumaluminosilicate, bariumfluoroaluminosilicate, strontiumfluoroaluminosilicate, strontiumzincfluoroaluminosilicate, zincaluminosilicate pre-polymerized composite filler, and any combination of one or more thereof. Examples of metal oxides and fluorides include, but are not limited to, barium oxide, strontium fluoride, barium fluoride, ytterbium fluoride, yttrium fluoride, zinc oxide, bismuth(III) oxide. In one embodiment, the said filler is treated with a coupling agent such as γ-methacryloyloxypropyltrimethoxysilane (MPTMS). In some instances, such treatment enhances the interfacial bonding between the filler and resin matrix, and improves mechanical properties.

In some embodiments, the filler is a finely divided filler, e.g., a filler comprising or comprised of a plurality of solid particles. In certain embodiments, the finely divided filler (e.g., particles thereof) has any suitable average dimension, such as, for example, an average size (e.g., particle size) of between 0.02 micron (μm) and 30 micron. In specific embodiments, the average size is between 0.2 micron and 10 micron.

In certain embodiments, the filler is present in a composition provided herein in any suitable amount. In some embodiments, the filler (e.g., finely divided filler) is present in the composition in an amount between 10 wt. % and 90 wt. %. In specific embodiments, the weight percentage is between 40% and 80%.

In certain embodiments, a composition (or part thereof) provided herein further comprises at least one photo-initiator. Any suitable photo-initiator(s) is optionally included. Examples of a photo-initiator include, but are not limited to, benzoin and derivatives, 2,2-diethoxy acetophenone, camphoroquinone, 1-phenyl-1,2-propanedione, monoacylphosphine oxide, bisacylphosphine oxide, and a mixture thereof. Additionally, an activator can be used together with a photo-initiator. Examples of activators include, but are not limited to, 2-ethyl-4-(N,N-dimethylamino) benzoate, 2-amyl-4-(N,N-dimethylamino) benzoate, 2-octyl-4-(N,N-dimethylamino) benzoate; 2-(ethylhexyl)-4-(N,N-dimethylamino) benzoate, N,N-dimethylaminoethyl methacrylate, N,N-dimethylaminophenethyl alcohol and a mixture thereof. In one embodiment, the photo-initiator system comprises camphoroquinone and a tertiary amine selected from the group of 2-ethyl-4-(N,N-dimethylamino) benzoate, 2-amyl-4-(N,N-dimethylamino) benzoate, 2-octyl-4-(N,N-dimethylamino) benzoate; 2-(ethylhexyl)-4-(N,N-dimethylamino) benzoate, N,N-dimethylaminoethyl methacrylate, N,N-dimethylaminophenethyl alcohol and any mixture of one or more thereof. In one embodiment, the weight percentage of the photo initiator is less than 5%. In one embodiment, the weight percentage of the photo initiator is less than 3%.

In certain embodiments, a composition provided herein comprises at least one stabilizer. In some instances, a stabilizer is an agent that inhibits polymerization, such as of the monomer component(s) of a composition described herein. In certain instances, such agents are useful for improving the shelf life of a composition provided herein (e.g., inhibiting polymerization of the monomer prior to use). Any suitable stabilizer, or polymerization inhibitor (such as a free radical scavenger), is optionally utilized herein. Stabilizers include, by way of non-limiting example, 2,6-di-(tert-butyl)-4-methylphenol (BHT) and 4-methoxyphenol (MEHQ). Any suitable amount of stabilizers is optionally utilized, such as less than 1 wt. %.

In certain embodiments, provided herein are methods of utilizing and manufacturing such compositions, such as in and for dental applications. In general instances, such compositions are prepared in a dentally acceptable manner (i.e., in a manner suitable for administration into the mouth (or tooth cavity thereof) of an individual, patient or person). In specific embodiments, provided herein is a method of administering a composition described herein to an individual, such as to restore a tooth of the individual. In specific embodiments, a composition described herein is provided, any parts thereof are combined to form a mixed composition (e.g., wherein the monomers of the compositions are being polymerized), administering the mixed composition to the individual (e.g., into a cavity of the individual), and curing the mixed composition (e.g., until set).

In specific embodiments, the method is utilized to restore a tooth (e.g., a tooth comprising a cavity). In some embodiments, the composition is administered to, delivered into, and/or used to restore a tooth comprising a Class I or Class II cavity (e.g., based on the G.V. Black classification system), or a cavity in a posterior tooth. In certain embodiments, a Class I cavity is a cavity located in a pit or fissure of the occlusal surfaces of molars and premolars, the occlusal two-thirds of the buccal surfaces of molars, the lingual surfaces of upper incisors, or in the lingual surfaces of upper molars. In some embodiments, a Class II cavity is a cavity in the proximal surface of a molar or premolar. In certain embodiments, the composition is particularly useful in providing an effective mechanism of filling large cavities—an area where other restoration compositions are lacking. In specific embodiments, a cavity treated according to a process herein has a depth of about 3 mm or more (e.g., about 4 mm or more, about 5 mm or more, about 5 mm to about 7 mm, or the like) from any surface of the tooth (e.g., the fill surface of the tooth, or where the surface of the tooth was prior to the cavity, or would have been in the absence of the cavity).

In some embodiments, the mixture is further cured by a dental curing light, e.g., after it sets at the intraoral conditions. In further or alternative embodiments, an additional layer of a dental composition provided herein is placed on top of the set or cured mixture followed by curing with a dental curing light.

In specific embodiments, the parts of a composition provided herein are mixed to form a mixed composition, the mixed composition being administered to an individual (e.g., a dental cavity of the individual), and the mixed composition being cured under ambient conditions (or, being allowed to self-cure) for up to 15 minutes (e.g., 0.2 minutes to 15 minutes, 0.5 minutes to 10 minutes, 1 minutes to 6 minutes, 2 minutes to 5 minutes, or 3 minutes to 4 minutes, and the like). In specific instances, curing under ambient conditions comprises allowing the composition to set (e.g., cure in the absence of a light initiator device, such as a device that emits light, a majority of which having a blue wavelength (e.g., in the 400-530 nm range, or about 470 nm)). In specific embodiments, the cured (e.g., self-cured or set) composite is further cured using a light initiator device, such as a device that emits light, a majority of which having a blue wavelength (e.g., in the 400-530 nm range, or about 470 nm). In more specific embodiments, prior to light curing, additional mixed composition is administered to the cavity. In some instances, light curing at the surface is desirable, to facilitate complete curing of the filling at the surface (e.g., wherein radical—e.g., of living polymer and/or initiator—groups may interact and die in the air prior to complete polymerization/curing).

In some embodiments, one or more of the desirable restorative material characteristics described herein is achieved in any suitable manner, such as by using the concentrations of materials described herein. In certain embodiments, provided herein is a composition (e.g., two part composition) comprising copper (II), such as described herein. In some embodiments, presence of the copper (II) catalyzes the curing (e.g., self-curing) of a composition at a rate sufficient to be dentally effective. In some embodiments, the amount of copper (II) (or compound thereof) present need not be much to have an effect. For example, in some embodiments, less than 0.1 wt. % or even less than 0.01 wt. % of copper (II) (or compound thereof) is utilized. In further or alternative embodiments, good curing rates are achieved using higher concentrations of hydroperoxide and/or thiourea. In some embodiments, a composition provided herein comprises a combined concentration of hydroperoxide and thiourea (e.g., the hydroperoxide and thiourea provided in separate parts of the composition) is about 2.5 wt. % (relative to the total weight of the monomer—i.e., {{wt. hydroperoxide+wt. thiourea}/total wt. monomer}*100%) or more, about 3 wt. % or more, about 4 wt. % or more, or about 5 wt. % or more.

Provided in certain embodiments herein is a dental cement comprising the cured combination of the first and second parts of any composition herein, or the cured combination of any composition comprising thiourea with any composition comprising a hydroperoxide described herein. In certain embodiments, one or both parts of a composition described herein comprise a copper (II) catalyst. In some embodiments, a composite provided herein comprises a cured resin (e.g., comprising polymerized monomer(s) described herein), filler and copper. In specific embodiments, the composite comprises cured resin in any suitable amount, such as an amount described herein for a composition comprising a monomer (e.g., about 10 wt. % to about 60 wt. %), the filler in any suitable amount, such as an amount described herein for a composition comprising the filler (e.g., about 10 wt. % to about 90 wt. %, and the copper in an amount of about 1 elemental wt. % or less (e.g., based on amount of copper present on an elemental basis) (e.g., about 0.1 wt. % or less, about 0.05 wt. % or less, or the like). In specific embodiments, the dental composite comprises filler in an amount of about 60% (w/w) to about 80% (w/w) and cured resin in an amount of about 20% (w/w) to about 40% (w/w).

In certain embodiments, the dental cement compositions provided and used herein have no to low acid and/or anhydride content. In specific embodiments, the acid and/or anhydride content is less than 5 wt. % of the composition. In more specific embodiments, the acid and/or anhydride content is less than 3 wt. % of the composition, less than 2 wt. % of the composition, less than 1 wt. % of the composition, less than 0.5 wt. %, less than 0.1 wt. % of the composition, or the like. In some embodiments, the composition has a substantially neutral or alkaline nature, such as a pH of about 5 or higher, a pH of about 5.5 of higher, a pH of about 6 or higher, a pH of about 6.5 or higher, or a pH of about 7 or higher. In specific instances, it is preferred that the acid content of the composition be minimized for any reason, such as to minimize hygroscopicity or water sorption of the resultant composite. In some instances, high levels of water sorption into the composite, when used as a restoration material, may result in volume expansion in the restoration material, which may lead to deformation of the restoration material, and, ultimately, dislodgement of the restoration material, damage to the tooth, and/or other undesirable outcomes.

In certain embodiments, a composition provided herein cures to a composite (or a composite provided herein has) a water sorption of about 100 $\mu g/mm^3$ or less. In specific embodiments, the water sorption is about 50 $\mu g/mm^3$ or less, about 25 $\mu g/mm^3$ or less, about 20 $\mu g/mm^3$ or less, or about 15 $\mu g/mm^3$.

In some embodiments, composites described herein (e.g., formed from the combination of the composition parts described herein) have good physical parameters for dental applications. In some embodiments, such composites have good flexural strength (e.g., greater than 50 MPa, greater than 100 MPa, greater than 125 MPa, or the like). In further or alternative embodiments, the composites have good compression strength (e.g., greater than 100 MPa, greater than 150 MPa, greater than 200 MPa, greater than 250 MPa, or the like). In certain embodiments, the composites have good diametral strength (e.g., greater than 30 MPa, greater than 40 MPa, greater than 45 MPa, or the like). In some embodiments, composites provided herein good water solubility (e.g., less than 1 $pig/mm^3$). In certain embodiments, the composites provided herein have good radiopacity (e.g., greater than 200% Al, greater than 300% Al, or the like). Any suitable process is optionally utilized to determine such parameters, such as testing a film comprising such a composite (e.g., the film having a thickness of about 10 microns to about 15 microns, such as about 14 microns).

Also provided herein are methods of manufacturing the compositions described herein. In some embodiments, the component parts of the compositions described herein are combined in any suitable order. Exemplary processes are set forth in the Examples. In specific embodiments, a part of a composition provided herein is prepared by combining monomer, hydroperoxide, optional stabilizer, and optional photoinitiator. In some embodiments, combination thereof is mixed to form a resin to which filler is added and blended or milled. Likewise, a part of a composition provided herein is, in specific embodiments, prepared by combining monomer, thiourea, optional stabilizer, and optional photoinitiator. In some embodiments, combination thereof is mixed to form a resin to which filler is added and blended or milled. Exemplification of specific agents (as well as the corresponding component class type) as set forth in the examples are to be understood as being included in the disclosure of compositions and methods described herein.

A ceramic is an inorganic, non-metallic, solid material comprising metal, non-metalormetalloidatoms primarily held in ionic and covalent bonds. In dentistry, ceramic materials have been widely used to fabricate dental crowns and typical ceramic materials include, but not limited to, zirconium oxide, feldspathic porcelain, lithiumdisilicate. In order to have good bonding strength on these materials, a primer may be needed prior to cementation.

A pre-cured dental resin may also be used to fabricate dental crowns and a primer may also be needed to generate sufficient bond strength.

In some embodiments, the method comprises steps: 1) applying a dental bonding primer on dentin and enamel, optionally followed by a curing activator, optionally curing the primer layer with a dental curing light; 2) applying a dental bonding primer on prefabricated restorations, such as crowns, inlays, onlays, veneers, optionally followed by a curing activator, optionally curing the primer layer with a dental curing light; and 3) applying a dental cement layer to bond prefabricated restorations to the tooth structure (dentin and enamel).

In some embodiments, the dental bonding primer comprises at least one polymerizable monomer with at least one phosphoric acid pendant group. In some embodiments, the monomer is selected from the group consisting of Ethylene glycol methacrylate phosphate, Bis [2-(methacryloyloxy) ethyl] phosphate, 10-Methacryloyloxydecyl dihydrogenphosphate, glycerol phosphate di(meth)acrylate, phenyl-P (phenyl methacryloxyethyl phosphate), PENTA-P (dipentaerithritolpentaacrylate phosphate).

In some embodiments, the dental bonding primer comprises at least one polymerizable monomer with at least one carboxylic acid or anhydride pendant group. In some embodiments, the monomer is selected from the group consisting of (meth)acrylic acid, maleic anhydride, trimellitic anhydride, 4-META (4-methacryloxyethyltrimellitic anhydride), maleic anhydride, trimellitic anhydride, 4-META (4-methacryloxyethyltrimellitic anhydride); PM-HEMA (addition product of pyromellitic acid anhydride and 2-hydroxyethyl methacrylate), PM-GDM (addition product of pyromellitic acid anhydride and glycerol dimethacrylate), BTDA-HEMA (addition product of 3,3',4,4'-benzophenonetetracarboxylic dianhydride and hydroxyethyl methacrylate), and PA-HEMA (addition product of phthalic anhydride and hydroxyethyl methacrylate), MA-GDM (addition product of maleic anhydride and glycerol dimethacrylate).

In some embodiments, the dental bonding primer comprises at least one ethylenically unsaturated group with at least one (meth)acrylate group. In specific embodiments, the ethylenically unsaturated group is selected from acrylate and methacrylate groups. Examples of polymerizable monomers include, but are not limited to, the following: glycerol di(meth)acrylate, glycerol mono(meth)acrylate, hydroxyethyl (meth)acrylate {(meth)acrylate=acrylate or methacrylate}, hydroxypropyl (meth)acrylate, methyl (meth)acrylate, ethyl (meth)acrylate, propyl (meth)acrylate, octyl (meth)acrylate, decyl (meth)acrylate, 2-ethoxyethyl (meth)acrylate, 2'-ethoxy-2-ethoxyethyl (meth)acrylate, ethyleneglycol di(meth)acrylate, diethyleneglycol di(meth)acrylate, triethyleneglycol di(meth)acrylate; polyethyleneglycol mono-(meth)acrylate, polyethyleneglycol di-(meth)acrylate, polypropyleneglycol mono-(meth)acrylate, polypropyleneglycol di-(meth)acrylate, polytetramethyleneglycol mono-(meth) acrylate, polytetramethyleneglycol di-(meth)acrylate, hexanediol di(meth)acrylate, octanediol di(meth)acrylate, decanediol di(meth)acrylate, trimethyloylpropane tri(meth) acrylate, urethane dimethacrylate (reaction adduct of 2-hydroxyethyl methacrylate with 2,4,4-trimethylhexane diisocyanate), 2,2-bis[4-(2-hydroxy-3-methacryloylpropoxy)-phenyl]-propane (Bis-GMA), ethoxylatedbisphenol A dimethacrylate (where total number of moles of ethylene oxide in the molecule may range from 2 to 30 units) in tetrahydrofurfuryl (meth)acrylate, or mixtures thereof. As referred to herein, "(meth)acrylate" includes disclosures of both methacrylate and acrylate.

In some embodiments, the dental bonding primer comprises at least one solvent. In some embodiments, the solvent is selected from the group consisting of ethanol, isopropanol, n-propanol, n-butanol, t-butanol, acetone, methyl ethyl ketone, water.

In some embodiments, the curing activator is a chemical that generates free radical at acidic environment.

In some embodiments, the material of the prefabricated restorations is a pre-cured dental resin material with at least one inorganic filler. In some embodiments, the material of the said prefabricated restorations is a ceramic. In some embodiments, the said ceramic is selected from the group consisting of zirconium oxide, feldspathic porcelain, lithium disilicate.

In some embodiments, the dental primer on prefabricated restorations is a dental bonding agent. In some embodiments, the dental primer is a primer that comprises at least one silane with at least one (meth)acrylate pendant group.

In some embodiments, the dental cement is delivered through a dental dual-barrel syringe equipped with a mixing tip onto the said prefabricated restorations.

In some embodiments, the excess of the dental cement is cleaned with a dental instrument. In some embodiments, the dental cement is optionally cured by a dental curing light.

In some instances, as used herein, a "set time" is the amount of time under which a mixed composition provided herein (i.e., a composition combining both parts of a two-part described composition described herein) forms a solid or hard composite (which is partially or completely cured), particularly in the absence of an ancillary device designed to facilitate the curing of restoration materials, such as a dental curing light (e.g., also referred to herein as "self-curing"). A dental curing light is a piece of dental equipment that is used for polymerization of light cure resin based composites. It can be used on several different dental materials that are curable by light. The light used falls under the visible blue light spectrum. This light is delivered over a range of wavelengths and varies for each type of device. There are four basic types of dental curing lights; Tungsten halogen, light-emitting diode (LED), plasma arc curing (PAC), and laser. In certain instances, the "work time" is the length of time after which the mixed composition ceases being malleable using typical dental techniques and/or equipment.

As used herein, weight percentage (wt. % or % (w/w)) refers, unless otherwise noted, the percentage of the weight of a component relative to the overall weight of a composition or composite. In some embodiments, the weight percentage refers to the weight of the component relative to the weight of a two part composition (e.g., wherein a first and second part are physically separated) and/or the weight of the component relative to the weight of one part of a two part composition. In some instances, the weight percentage of the component may be identical or similar in both parts of the two part system, and in other instances, the component may have different weight percentages in each part of the two part system. For example, in general instances, the hydroperoxide and thiourea each have different weight percentages in each of the parts, with the hydroperoxide being wholly or primarily in a first part of the composition and the thiourea being wholly or primarily in a second part of the composition.

The term "alkyl" as used herein, alone or in combination, refers to an optionally substituted straight-chain, or optionally substituted branched-chain saturated or unsaturated hydrocarbon monoradical having, e.g., from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "$C_1$-$C_6$ alkyl," means that in some embodiments, the alkyl group consists of 1 carbon atom; in some embodiments, 2 carbon atoms; in some embodiments, 3 carbon atoms; in some embodiments, 4 carbon atoms; in some embodiments, 5 carbon atoms; or, in some embodiments, 6 carbon atoms, although the present definition also covers the occurrence of the term "alkyl" where no numerical range is designated. In addition, in some instances, such as wherein the alkyl is substituted on either side (e.g., as set forth for L above), the alkyl may refer to a diradical derived from the above-defined monoradical, alkyl. Examples include, but are not limited to methylene (—$CH_2$—), ethylene (—$CH_2CH_2$—), propylene (—$CH_2CH_2CH_2$—), isopropylene (—$CH(CH_3)CH_2$—) and the like. An "alkyl" may also refer to a cyclic alkyl group, referring to an optionally substituted, saturated, hydrocarbon monoradical ring, containing, e.g., from three to about fifteen ring carbon atoms or from three to about ten ring carbon atoms, though, in some embodiments, includes additional, non-ring carbon atoms as substituents (e.g. methylcyclopropyl). The term includes fused, non-fused, bridged and spiro radicals. In some embodiments, a fused cycloalkyl contains from two to four fused rings where the ring of attachment is a cycloalkyl ring. Examples include, but are not limited to cyclopropyl, cyclopentyl, cyclohexyl, cumene, and pinanering systems.

The term "aryl" as used herein, alone or in combination, refers to an optionally substituted aromatic hydrocarbon radical of six to about twenty ring carbon atoms, and includes fused and non-fused aryl rings. A fused aryl ring radical contains from two to four fused rings where the ring of attachment is an aryl ring, and the other individual rings are alicyclic, heterocyclic, aromatic, heteroaromatic or any combination thereof. Further, the term aryl includes fused and non-fused rings containing from six to about twelve ring carbon atoms, as well as those containing from six to about ten ring carbon atoms. A non-limiting example of a single ring aryl group includes phenyl; a fused ring aryl group includes naphthyl, phenanthrenyl, anthracenyl, azulenyl; and a non-fused bi-aryl group includes biphenyl.

The term "heteroaryl" as used herein, alone or in combination, refers to optionally substituted aromatic monoradicals containing from about five to about twenty skeletal ring atoms, where one or more of the ring atoms is a heteroatom independently selected from among oxygen, nitrogen, and sulfur, but not limited to these atoms and with the proviso that the ring of said group does not contain two adjacent O or S atoms. In embodiments in which two or more heteroatoms are present in the ring, the two or more heteroatoms are the same as each another, or some or all of the two or more heteroatoms are different from the others. The term heteroaryl includes optionally substituted fused and non-fused heteroaryl radicals having at least one heteroatom. The term heteroaryl also includes fused and non-fused heteroaryls having from five to about twelve skeletal ring atoms, as well as those having from five to about ten skeletal ring atoms. In certain instances, bonding to a heteroaryl group is via a carbon atom or a heteroatom. A non-limiting example of a single ring heteroaryl group includes pyridyl or furanyl.

The term "heteroalkyl" as used herein, refers to optionally substituted alkyl structure, as described above, in which one or more of the skeletal chain carbon atoms (and any associated hydrogen atoms, as appropriate) are each independently replaced with a heteroatom (i.e. an atom other than carbon, such as though not limited to oxygen, nitrogen, sulfur, or combinations thereof). Exemplary heteroalkyl groups include straight chain groups, such as ethylene oxides (e.g., —CH2CH2On-), or ringed groups, such as tetrahydrofuran.

EXAMPLES

Abbreviations for materials used in the examples include, as follows:
PTU: 1-(2-Pyridyl)-2-thiourea
CHP: Cumene hydroperoxide
CuPD: Copper(II) acetylacetonate
MDP: 10-Methacryloyloxydecyl dihydrogen phosphate
R202: AEROSIL® fumed silica
R812S: AEROSIL® fumed silica
GM27884-K6: Schott GM27884 Dental Glass, 3 μm
YbF3: Ytterbium Fluoride
BYK W9010: Wetting and dispersing additive (flow modifier)
CQ: Camphorquinone
EDMAB: Ethyl-4-dimethylamino benzoate
UDMA: Urethane dimethacrylate
E6BAD: Ethoxylated (6) Bisphenol A Dimethacrylate
EBPADM: Ethoxylated (3) Bisphenol A Dimethacrylate
BisGMA: Bisphenol A-glycidyl methacrylate
TEGDM: Triethylene glycol dimethacrylate
BHT: Butylatedhydroxytoluene
HDK N-20P: Fumed silica
Pluronic L-44: Surfactant
DI water: Distilled water
DHEPT: N—N-bis(2-hydroxyethyl)-P-toluidine
BPO: Benzoyl peroxide Examples 1—Preparing a Bonding Agent Having 16% MDP Examples 1 and 2 were prepared by adding and mixing chemicals. All chemicals were mixed until all solids, except fumed silica, were dissolved, resulting in low viscosity liquid.

|  | Example 1 |
| --- | --- |
| BisGMA | 23.4 |
| HEMA | 15.6 |
| EDMAB | 0.7 |
| CQ | 0.5 |
| BHT | 0.04 |
| HDK N-20P | 3.6 |
| MDP | 16 |
| Pluronic L-44 | 0.1 |
| DI Water | 5 |
| Ethanol | 35 |
| Total | 99.94 |

Example 2—Preparing a Bonding Agent Having 8% MDP and 8% PMDM

Example 2 was prepared by mixing Example 1 and 2 in proportions.

|  | Example 2 |
| --- | --- |
| BisGMA | 23.4 |
| HEMA | 15.6 |
| EDMAB | 0.7 |
| CQ | 0.5 |
| BHT | 0.04 |
| HDK N-20P | 3.6 |
| MDP | 8 |
| PMDM | 8 |
| Pluronic L-44 | 0.1 |
| DI Water | 5 |
| Ethanol | 35 |
| Total | 99.94 |

Comparative Example A—Preparing a Bonding Agent Having 0% MDP and 16% PMDM

Examples 1 and 2 were prepared by adding and mixing chemicals. All chemicals were mixed until all solids, except fumed silica, were dissolved, resulting in low viscosity liquid.

|  | Comparative Example A |
| --- | --- |
| BisGMA | 23.4 |
| HEMA | 15.6 |
| EDMAB | 0.7 |
| CQ | 0.5 |
| BHT | 0.04 |
| HDK N-20P | 3.6 |
| PMDM | 16 |
| BYK W9010 | 0.1 |
| DI Water | 5 |
| Ethanol | 35 |
| Total | 99.94 |

Example 3-Preparing a First Part CHP-Coinitiator-Containing Paste

Example 3 was prepared by adding and mixing chemicals. Resin chemicals were mixed together with dissolvable solids, including CQ, EDMAB and BHT, until all solids were dissolved. Solid fillers, including R812S, YbF3 and GM27884 were then added and mixed by a speed mixer and followed by a three-roll mill, resulting in a paste-like semi-solid.

|  | Example 3 |
| --- | --- |
| E6BAD | 5.8 |
| BISGMA | 3.4 |
| TEGDM | 6.1 |
| UDMA | 2.6 |
| EBPADM | 10.3 |
| EDMAB | 0.06 |
| CQ | 0.02 |
| BYK-W 9010 | 0.1 |
| BHT | 0.03 |
| CHP | 0.6 |
| R812S | 1 |
| YbF3 | 9 |
| GM27884-K6 | 61 |
| Total | 100.01 |

Example 4—Preparing a Second Part PTU-Coinitiator-Containing Paste

Example 4 was prepared by adding and mixing chemicals. Resin chemicals were mixed together with dissolvable solids, including CQ, EDMAB, PTU and BHT, until all solids were dissolved. CuPD was added to a mixer of TEGDMA and mixed by a speed mixer. Solid fillers, including R812S, YbF3, and GM27884 were then added and mixed by a speed mixer, followed by a three-roll mill, resulting in a paste-like semi-solid.

|  | Example 4 |
| --- | --- |
| E6BAD | 5.6 |
| BISGMA | 3.4 |
| TEGDM | 5.9 |
| UDMA | 2.54 |
| EBPADM | 10 |
| EDMAB | 0.06 |
| CQ | 0.025 |
| BYK-W 9010 | 0.1 |
| BHT | 0.03 |
| PTU | 0.3 |
| CuPd | 0.0005 |
| R202 | 0.01 |
| YbF3 | 9 |
| R812S | 1 |
| GM27884-K6 | 62 |
| Total | 99.97 |

Example 5—Preparing Mixture of a First Part Example 3 Paste and a Second Part Example 4 Paste Example 5 was prepared by packing Examples 3 (CHP-coinitiator-containing) and 4 (PTU-coinitiator-containing) into a dual-barrel syringe, with each barrel hosting one respective paste as a First Part and Second Part. When this combination of pastes is used, a mixing tip is attached so that both pastes can pass through a mixing chamber and have proper mixing. Upon mixing, the material will harden over the time period of about 4 to 8 minutes.

Example 7 and 8 and Comparative Example B—Application of Bonding Agent and Mixed First and Second Parts Cement Paste Zirconia substrates were embedded into polymer resin and exposed by trimming off the top layer. Substrates were exposed and polished with 600 grit SiC paper. Zirconia surfaces were further sandblasted with 50 nm aluminum oxide powders at a pressure of 60 psi. All specimens were then thoroughly rinsed. A layer of bonding agent from either Example 1 or 2 or Comparative Example A was applied with light brushing motion, followed by air thinning for about 10 seconds. The specimen was then placed into a bonding jig that is described in ISO 29022-2013. The paste mixture of Example 5 was injected into the cavity and kept in a 35° C. humidity chamber for one hour before it was taken off the jig. The specimen was then placed in water and kept at an oven at 37° C. for 20 hours. The bond strength of the specimen was then recorded according to ISO 29022-2013. With 10 specimens of each group, the average bond strength and standard deviation are recorded in Table 1. The results indicate that the MDP containing bonding agents at either 16% (Example 1) or 8% (Example 2) provide bond strengths above 15 MPa at 19.8 MPa and 19.1 MPa, respectively; whereas the bonding agent in comparative Example A lacking MDP has inferior bond strength below 15 MPa at 11.6 MPa.

TABLE 1

Bond strength and standard deviations

|  | Example 7 | Example 8 | Comparative Example B |
|---|---|---|---|
| Bonding agents | Example 1 | Example 2 | Comparative Example A |
| Cement pastes | Example 5 | Example 5 | Example 5 |
| Bond strength (MPa) | 19.8 | 19.1 | 11.6 |
| Standard deviation | 3.2 | 4.3 | 4.0 |

Comparative Example C—Preparing a First Part BPO-Coinitiator-Containing Paste

Comparative Example C was prepared by adding and mixing chemicals as done in Example 3. Resin chemicals were mixed together with dissolvable solids, including CQ, EDMAB, BPO and BHT, until all solids were dissolved. Solid fillers, including R812S, YbF3 and GM27884 were then added and mixed by a speed mixer, followed by a three-roll mill, resulting in a paste-like semi-solid.

|  | Comparative Example C |
|---|---|
| E6BAD | 5.6 |
| BISGMA | 3.4 |
| TEGDM | 6.1 |
| UDMA | 2.6 |
| EBPADM | 10.4 |
| EDMAB | 0.06 |
| CQ | 0.023 |
| BYK-W 9010 | 0.15 |
| BHT | 0.03 |
| BPO | 0.6 |
| R812S | 1 |
| YbF3 | 9 |
| GM27884-K6 | 61 |
| Total | 99.963 |

Comparative Example D—Preparing a Second Part DHEPT-Coinitiator-Containing Paste Comparative Example D was prepared by adding and mixing chemicals as done in Example 4. Resin chemicals were mixed together with dissolvable solids, including CQ, EDMAB, DHEPT and BHT, until all solids were dissolved. Solid fillers, including R812S, YbF3 and GM27884 were then added and mixed by a speed mixer, followed by a three-roll mill, resulting in a paste-like semi-solid.

|  | Comparative Example D |
|---|---|
| E6BAD | 5.6 |
| BISGMA | 3.3 |
| TEGDM | 5.9 |
| UDMA | 2.5 |
| EBPADM | 10 |
| EDMAB | 0.06 |
| CQ | 0.023 |

-continued

|  | Comparative Example D |
|---|---|
| BYK-W 9010 | 0.14 |
| BHT | 0.03 |
| DHEPT | 0.6 |
| YbF3 | 9 |
| R812S | 1 |
| GM27884-K6 | 61.9 |
| Total | 100.053 |

Comparative Example E—Preparing Mixture of a First Part Example C Paste and a Second Part Example D Paste Comparative Example E was prepared as done in Example 5 by packing Comparative Examples C and D into a dual-barrel syringe, with each barrel hosting one paste. When this combination of pastes is used, a mixing tip is attached so that both pastes can pass through a mixing chamber and have proper mixing. Upon mixing, the material will harden over the time period of about 4 to 8 minutes.

Comparative Example F and G—Application of Bonding Agent and Mixed First and Second Parts Cement Paste As done in Examples 7 and 8, Zirconia substrates were embedded into polymer resin and exposed by trimming off the top layer. Substrates were exposed and polished with 600 grit SiC paper. Zirconia surfaces were further sandblasted with 50 nm aluminum oxide powders at a pressure of 60 psi. All specimens were then thoroughly rinsed. A layer of Example 1 or 2 was applied with light brushing motion, followed by air thinning for about 10 seconds. The specimen was then placed into a bonding jig that is described in ISO 29022-2013. The paste mixture of Comparative Example E was injected into the cavity and kept in a 35° C. humidity chamber for one hour before it was taken of the jig. The specimen was then placed in water and kept at an oven at 37° C. for 20 hours. The bond strength of the specimen was then recorded according to ISO 29022-2013. With 10 specimens of each group, the average bond strength and standard deviation are recorded in Table 2. The results shown in Table 2 indicate that when BPO (Example C) and DHEPT (Example D) are used as coinitiators in the First Part and Second Part coinitiator-containing-paste for preparing the cement paste, the bond strengths are much lower and weaker at 8.1 MPa and 11.4 MPa than when CHP (Example 3) and PTU (Example 4) at 19.8 MPa and 19.1 MPa, respectively, are used as coinitiators in the First Part and Second Part.

TABLE 2

Bond strength and standard deviations

|  | Comparative Example F | Comparative Example G |
|---|---|---|
| Bonding agents | Example 1 | Example 2 |
| Cement pastes | Comparative Example E | Comparative Example E |
| Bond strength | 8.1 | 11.4 |
| Standard deviation | 3.3 | 3.7 |

What is claimed is:

1. A dental composition, wherein said composition comprises, on a surface of a dental substrate,
    a bonding agent; and
    a paste mixture, wherein the paste mixture was formed by mixing together a previously separated first part and a second part, and wherein the first part comprises at least one polymerizable monomer and at least one hydroperoxide, wherein the hydroperoxide is Cumene hydroperoxide (CHP); and the second part comprises at least one thiourea compound, wherein the thiourea is 1-(2-Pyridyl)-2-thiourea (PTU); and
    wherein the bonding agent comprises 8% to 16% of 10-Methacryloyloxydecyl dihydrogen phosphate (10-MDP); wherein either the first part or second part of the paste mixture further comprises a copper (II) compound, and wherein bond strength of the dental bonding agent on a dental substrate is more than 15 MPa.

2. The dental composition of claim 1, wherein the dental substrate is Zirconia.

3. The dental composition of claim 1, wherein the bonding agent is a single bottle bonding agent.

4. A method of dental restoration, wherein said method comprises:
    a first step of applying a dental bonding agent on a dental substrate, wherein the bonding agent comprises at least one phosphoric acid containing (meth)acrylic monomer, wherein said phosphoric acid containing (meth)acrylic monomer is 10-Methacryloyloxydecyl dihydrogen phosphate (10-MDP); and a second step of applying paste mixture from a device having a first part and a second part separate from each other, wherein said first part and second part form the paste mixture, and wherein the paste mixture from the device comprises at least one polymerizable monomer and at least one hydroperoxide in the first part, wherein the hydroperoxide is Cumene hydroperoxide (CHP); and at least one thiourea compound in the second part, wherein said thiourea is 1-(2-Pyridyl)-2-thiourea (PTU), wherein either the first part or second part of the paste mixture further comprises a copper (II) compound, and wherein bond strength of the dental bonding agent on a dental substrate is more than 15 MPa.

5. The method of claim 4, wherein the bonding agent bonds effectively on a dental substrate.

6. The method of claim 4, wherein the dental substrate is Zirconia.

7. The method of claim 4, wherein the device is a dual-barrel syringe.

8. The dental composition of claim 1, wherein the previously separated first part and a second part were separated in a dual-barrel syringe.

* * * * *